(12) United States Patent
Consolaro et al.

(10) Patent No.: US 12,246,127 B2
(45) Date of Patent: Mar. 11, 2025

(54) PRE-FILLED CONTAINER, METHOD OF USE AND RELATED PRODUCTION METHOD

(71) Applicant: Brevetti Angela S.r.l., Vicenza (IT)

(72) Inventors: Francesco Federico Consolaro, Vicenza (IT); Edoardo Consolaro, Vicenza (IT); Rajeev Kabbur, Vicenza (IT); Angelo Consolaro, Vicenza (IT); Roberto Consolaro, Vicenza (IT)

(73) Assignee: Brevetti Angela S.r.l., Arzignano (IT)

( * ) Notice: Subject to any disclaimer, the term of this patent is extended or adjusted under 35 U.S.C. 154(b) by 183 days.

(21) Appl. No.: 17/912,082

(22) PCT Filed: Mar. 17, 2021

(86) PCT No.: PCT/IT2021/050071
§ 371 (c)(1),
(2) Date: Sep. 16, 2022

(87) PCT Pub. No.: WO2021/186485
PCT Pub. Date: Sep. 23, 2021

(65) Prior Publication Data
US 2023/0158255 A1    May 25, 2023

(30) Foreign Application Priority Data
Mar. 18, 2020    (IT) .......................... 102020000005764

(51) Int. Cl.
*B29C 49/20*    (2006.01)
*A61M 11/00*    (2006.01)
(Continued)

(52) U.S. Cl.
CPC ......... *A61M 11/008* (2014.02); *B01F 25/105* (2022.01); *B01F 25/4521* (2022.01);
(Continued)

(58) Field of Classification Search
CPC ............... B01F 25/105; B01F 35/7139; B65D 81/3255; B29L 2031/712; B29C 49/06; B29C 53/452
See application file for complete search history.

(56) References Cited

U.S. PATENT DOCUMENTS

| 4,950,237 A | 8/1990 | Henault et al. |
| 2012/0167528 A1* | 7/2012 | Consolaro ............... B29C 49/76 29/527.1 |

FOREIGN PATENT DOCUMENTS

| EP | 0315440 | 5/1989 |
| EP | 0417998 | 3/1991 |

(Continued)

OTHER PUBLICATIONS

International Search Report and the Written Opinion Dated May 11, 2021 From the International Searching Authority Re. Application No. PCT/IT2021/050071. (12 Pages).

(Continued)

*Primary Examiner* — Seyed Masoud Malekzadeh
*Assistant Examiner* — Debjani Roy

(57) ABSTRACT

This invention relates to a container (1) which is pre-filled or pre-fillable with one or more substances, such as a medical liquid and similar, comprising a squeezable activation compartment (2) intended to contain said one or more substances, a dispensing compartment (3) including a first portion (31) equipped with at least one dispensing member (311, 312, 314) of said one or more substances, and a second portion (32), wherein said second portion (32) of said dispensing compartment (3) and said activation compartment (2) are fluid-dynamically connected, and an activator element (4) arranged inside said container (1).
This invention also relates to a method for dispensing at least one substance by means of a container (1), and to a production method of a container (1).

23 Claims, 5 Drawing Sheets

(51) Int. Cl.
  *B01F 25/00* (2022.01)
  *B01F 25/452* (2022.01)
  *B01F 35/71* (2022.01)
  *B29C 49/42* (2006.01)
  *B65D 25/08* (2006.01)
  *B65D 81/32* (2006.01)
  *B01F 101/00* (2022.01)
  *B29C 49/46* (2006.01)
  *B29L 31/00* (2006.01)

(52) U.S. Cl.
  CPC .......... *B01F 35/7139* (2022.01); *B29C 49/20* (2013.01); *B29C 49/42809* (2022.05); *B65D 25/082* (2013.01); *B65D 81/3255* (2013.01); *A61M 2205/075* (2013.01); *A61M 2205/273* (2013.01); *A61M 2207/00* (2013.01); *A61M 2210/0618* (2013.01); *B01F 2101/2202* (2022.01); *B29C 2049/2008* (2013.01); *B29C 49/46* (2013.01); *B29C 2049/4664* (2013.01); *B29L 2031/712* (2013.01)

(56) References Cited

FOREIGN PATENT DOCUMENTS

| | | |
|---|---|---|
| EP | 0509754 | 10/1992 |
| EP | 0905049 | 3/1999 |
| GB | 2235897 | 3/1991 |
| JP | H02-4675 | 1/1990 |
| JP | H03-151222 | 6/1991 |

OTHER PUBLICATIONS

Rapporto di Ricerca e l'Opinione Scritta [Search Report and the Written Opinion] Dated Nov. 18, 2020 From the Ministero Dello Sviluppo Economico, Direzione Generale Sviluppo Produttivo e Competitivita, Ufficio Italiano Brevetti e Marchi Re. Application No. IT202000005764. (10 Pages).

* cited by examiner

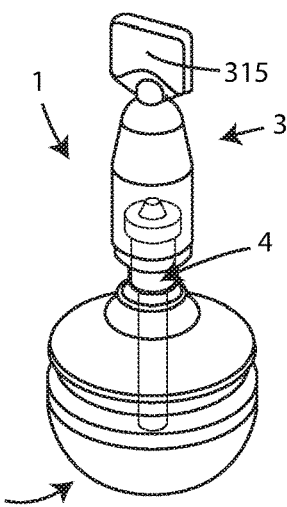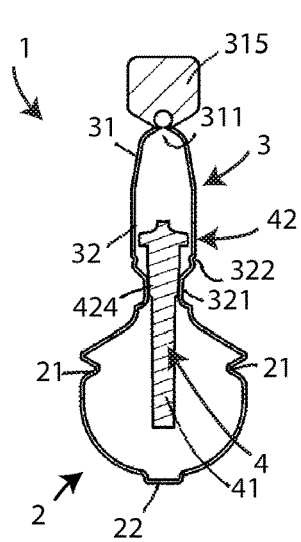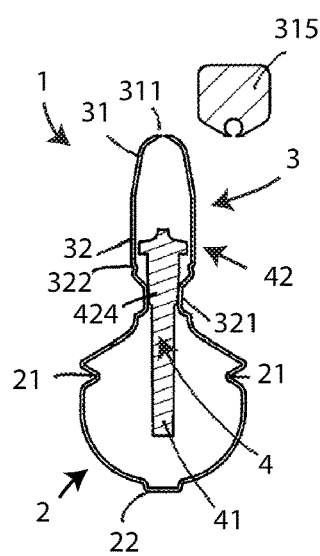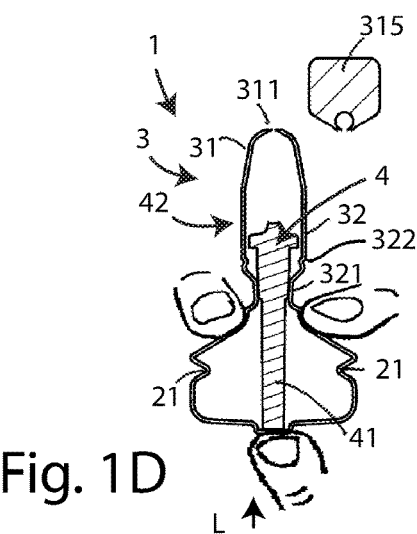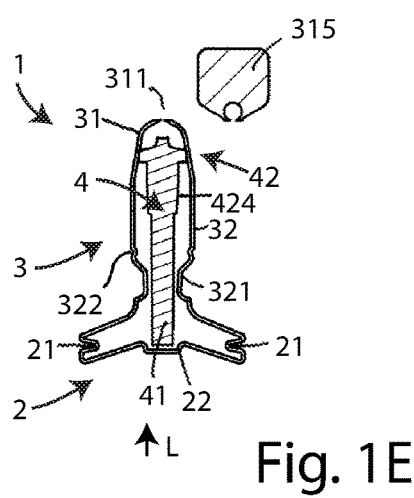
Fig. 1A
Fig. 1B
Fig. 1C
Fig. 1D
Fig. 1E

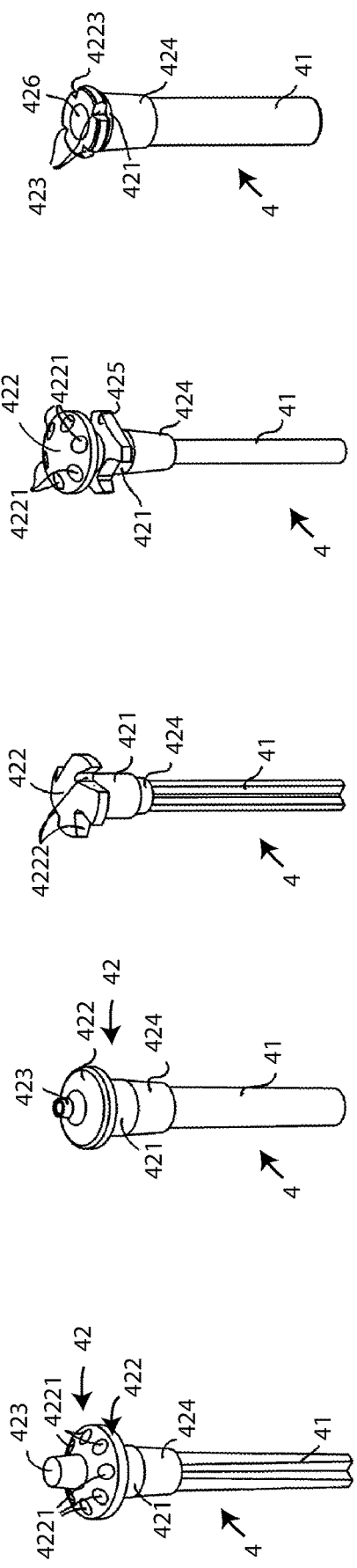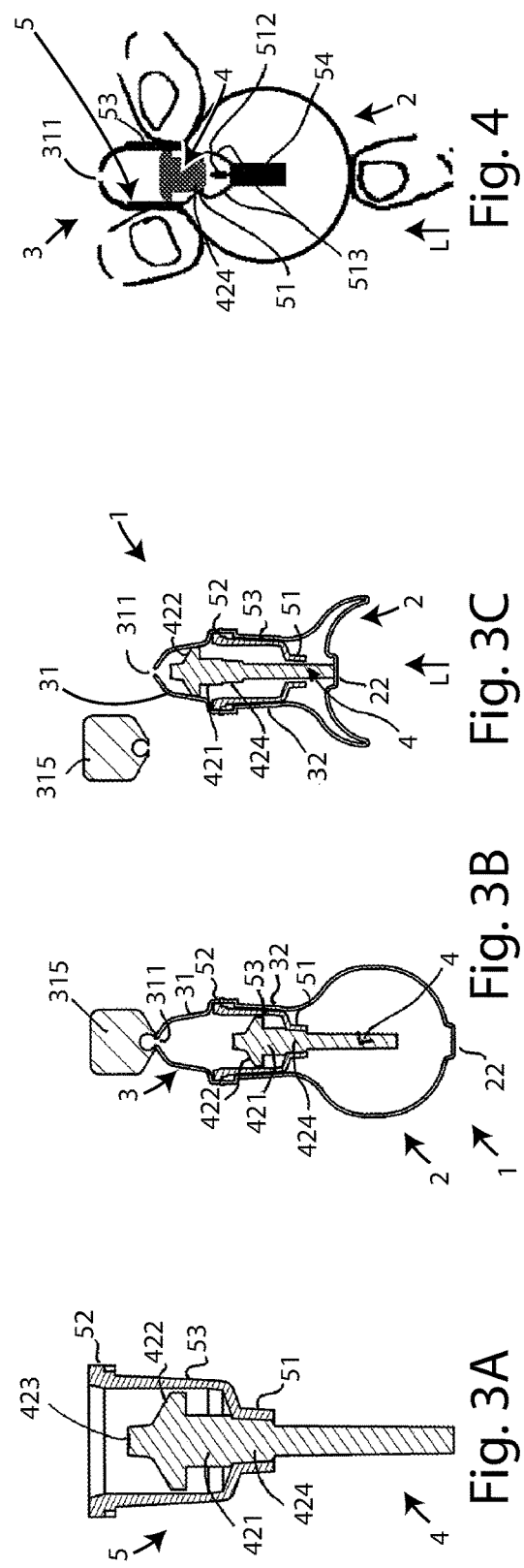

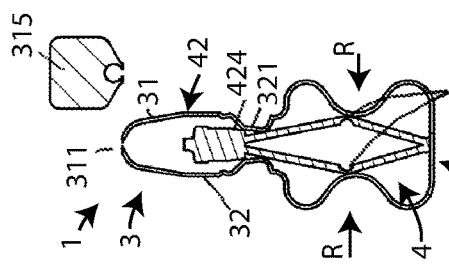
Fig. 5A
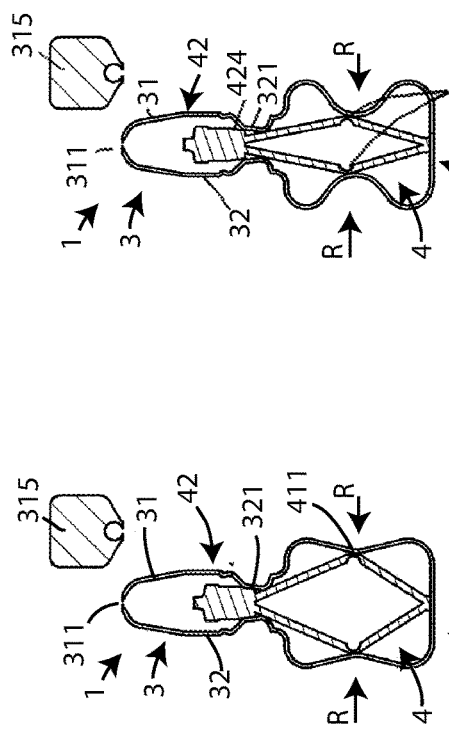
Fig. 5B
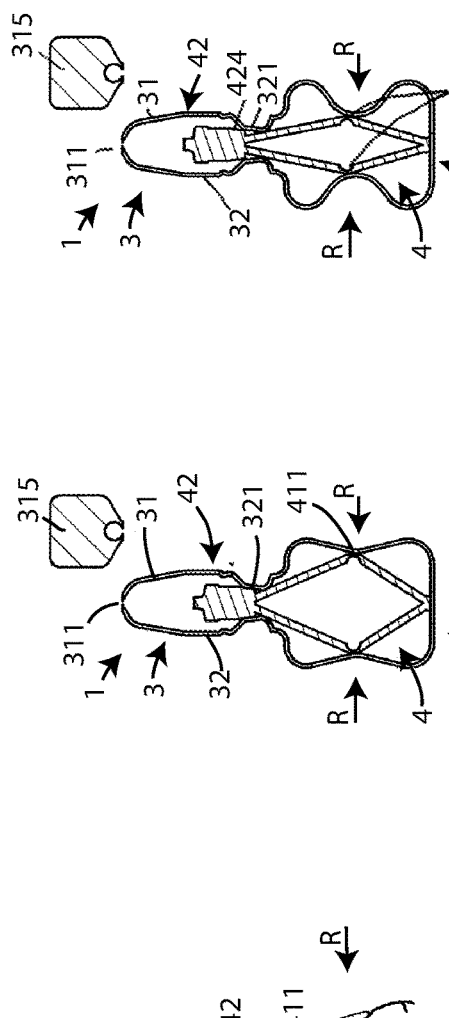
Fig. 5C
Fig. 5D
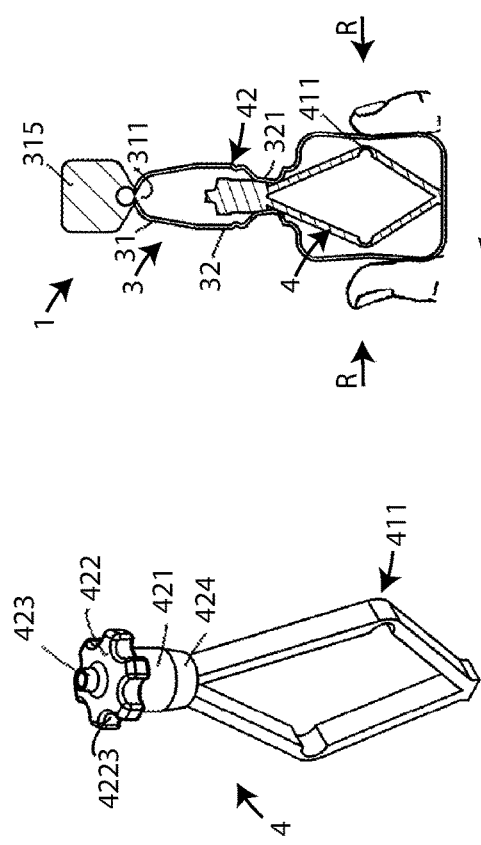
Fig. 6A
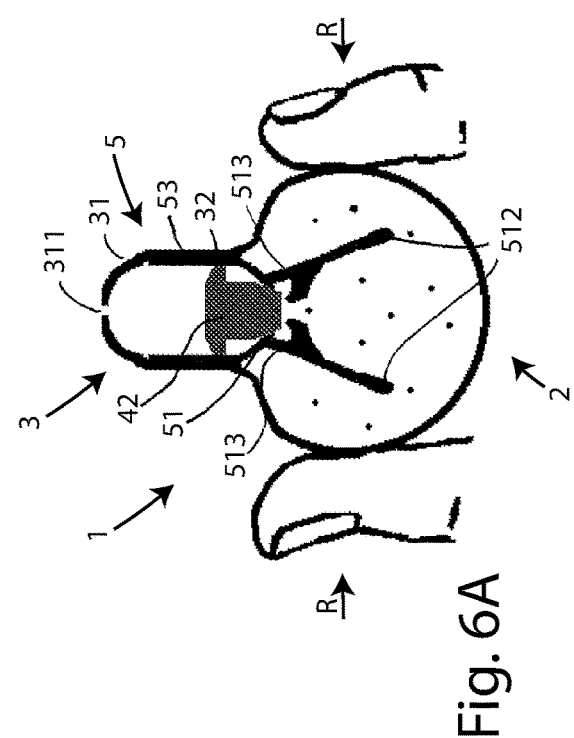
Fig. 6B

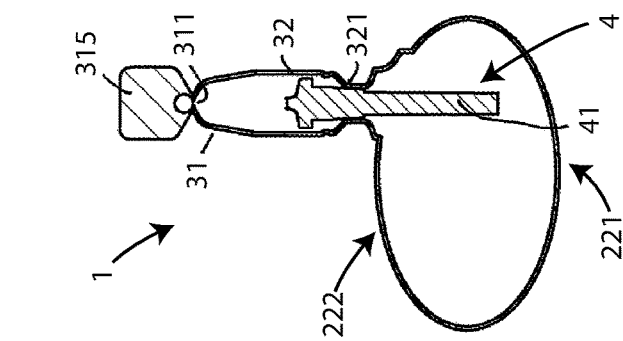
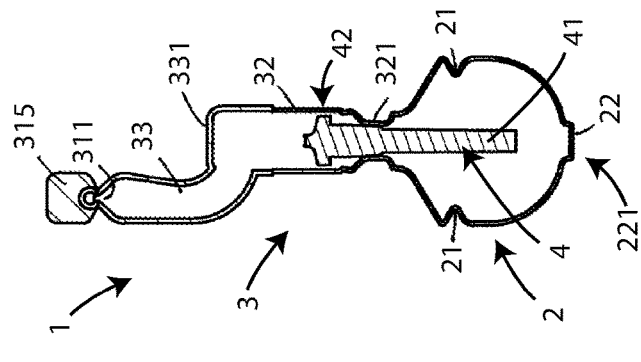
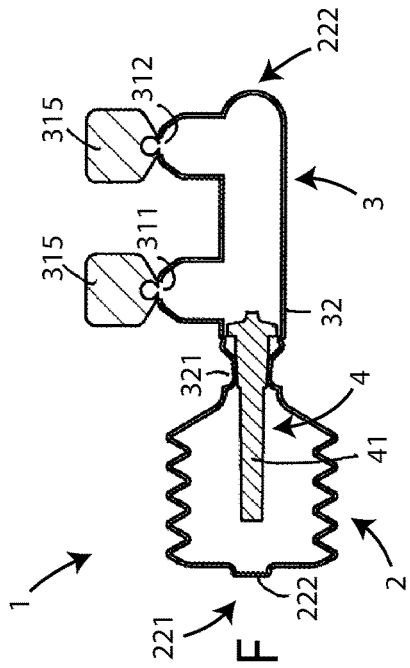
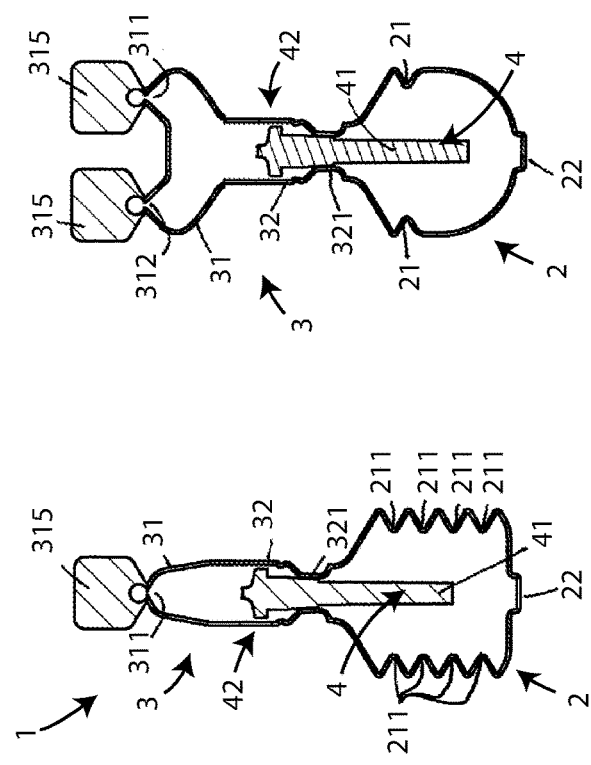
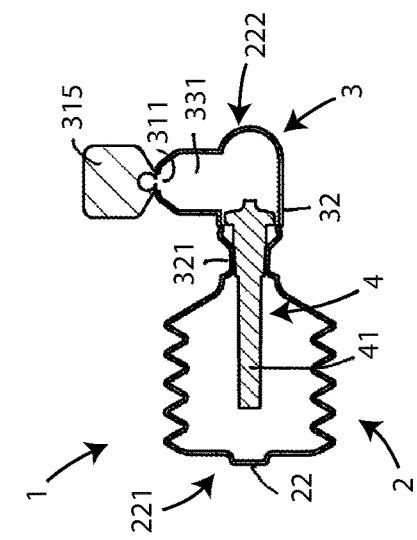

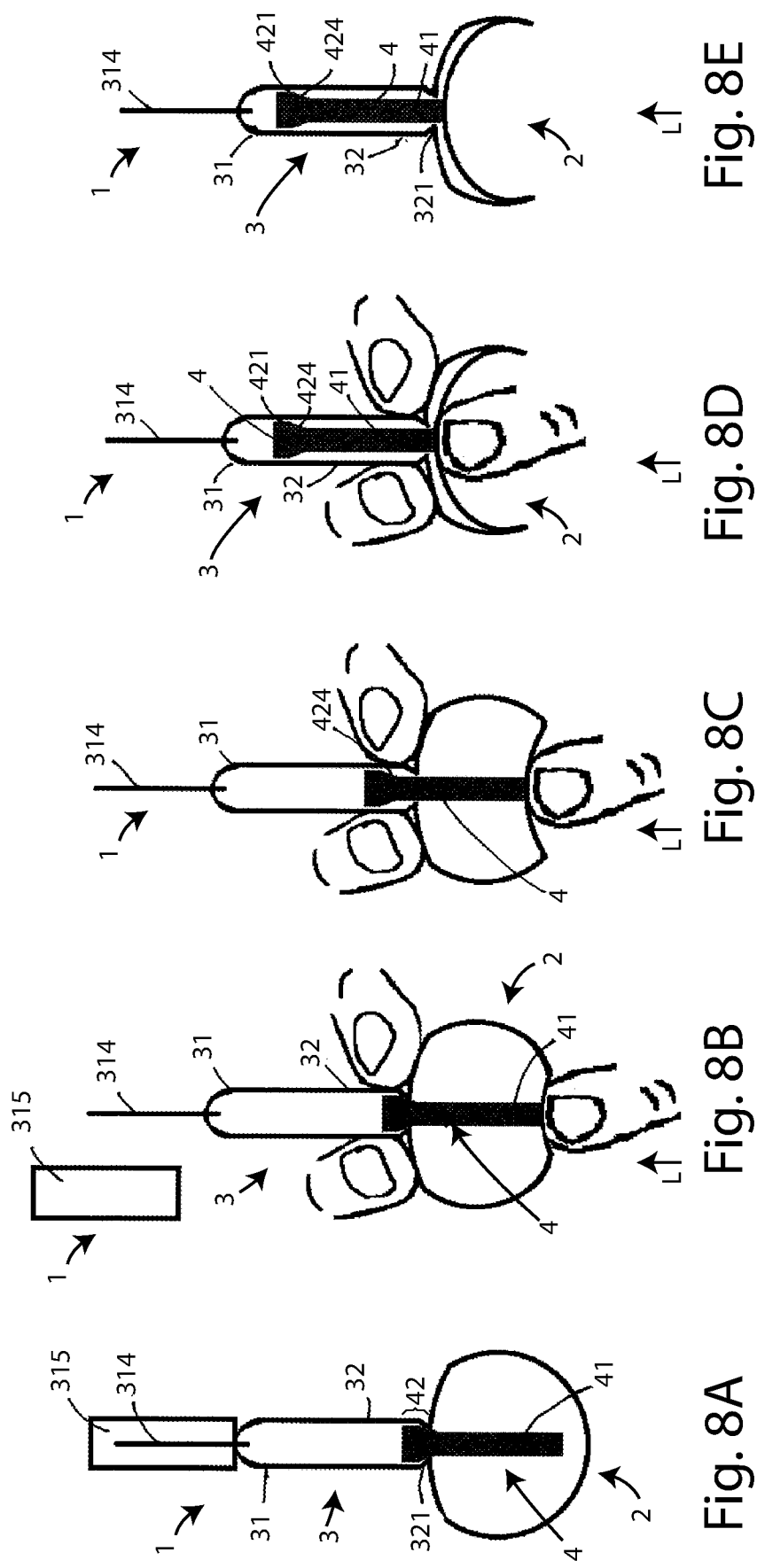

PRE-FILLED CONTAINER, METHOD OF USE AND RELATED PRODUCTION METHOD

RELATED APPLICATIONS

This application is a National Phase of PCT Patent Application No. PCT/IT2021/050071 having International filing date of Mar. 17, 2021, which claims the benefit of priority of Italian Patent Application No. 102020000005764 filed on Mar. 18, 2020. The contents of the above applications are all incorporated by reference as if fully set forth herein in their entirety.

This invention relates to a pre-filled container, a method of use and a relative production method.

FIELD AND BACKGROUND OF THE INVENTION

In more detail, the invention relates to a pre-filled container which allows the contents of at least two compartments to be mixed at the time of dispensing, so as to ensure the isolation of the substances to be dispensed until the time of actual use.

Further, the above-mentioned invention relates to a pre-filled container which is easy to use, while ensuring accuracy in the release of the contents, and avoiding, to the greatest extent possible, possible contamination.

This system makes it possible to create products with different uses and purposes operating under the same principle according to this invention.

As is known, spray devices for dispensing substances are widely used in the medical sector, especially when the substances to be dispensed have to be sterile and/or are dangerous, or even for particularly expensive substances or substances whose dispensing is permitted in specific dosages.

One problem with the above-mentioned type of pre-filled containers is that they are made up of several parts which require assembly, often with metal components, which considerably increases the cost thereof.

A further problem with medical sprays is the difficulty in producing a consistent size of the atomised droplets of medicine in the three phases of drug use, i.e.: droplet formation phase, full development phase, and dissipation phase.

Another common use of these containers is for pre-filled syringes.

There is currently no affordable, sterile system on the market that allows needle and product to be kept separate for long shipping and storage periods, and that is sterile until it is activated.

Further, there are currently no known affordable mechanisms in the field which, if required, would also prevent the reuse of the container after an initial dispensing of the product.

SUMMARY OF THE INVENTION

Within the above-mentioned requirements therefore, the main aim of this invention is to propose a pre-filled container, for example of one or more given medicaments, capable of overcoming the technical drawbacks mentioned above and in particular, to make a pre-filled container that is safe to use, whatever the shape thereof.

A further aim of this invention is to make a pre-filled container which is capable of dispensing drops of medicine like a spray.

Further, it is an aim of this invention to make a pre-filled container which, if required, guarantees the non-reusability by the user or by third parties.

Another aim of this invention is to make a pre-filled container adapted to allow a safe use in a number of respects: hygiene, accuracy in releasing the drug and intrinsic safety for the patient and the operator.

Furthermore, it is an aim of this invention to make a pre-filled container adapted to be used for making standard syringes, vials, or other medical or non-medical containers, etc. . . . .

A further aim of this invention is to make a pre-filled container which is functional, quick to implement and sufficiently accurate in releasing the medication.

The aim of this invention is therefore to create an effective product in terms of cost, ease of production, use, safety and, in addition, to guarantee sterility up to the moment of use.

These and other aims are achieved by a pre-filled container according to the invention, as will better emerge later in this description.

Thus, the object of this invention is a container which is pre-filled or pre-fillable with one or more substances, such as a medical liquid and similar, wherein the container may comprise a squeezable activation compartment intended to contain the aforesaid one or more substances, a dispensing compartment in turn comprising a first portion equipped with at least one dispensing member for dispensing the substances contained therein, and a second portion at which the dispensing compartment and the activation compartment are fluid-dynamically connected; the container also comprises therein a movable activator element adapted to pass from a closed position, wherein it hermetically and/or fluid-dynamically isolates the contents of the activation compartment from the contents of the dispensing compartment, to an open position, wherein it puts them into communication, thus allowing the substances to be dispensed through the dispensing member.

In a preferred variant of the invention, the activator element passes from the closed position to the open position when the activation compartment is squeezed.

Further, the activation compartment is configured so that when squeezed, it interferes with the activator element to allow the movement thereof.

In addition, the activator element comprises a tapered closing portion configured to engage between the activation compartment and the dispensing compartment of the container.

Further, the activator element may comprise a head bottomly coupled with a closing portion, and a stem in turn bottomly coupled with respect to the closing portion itself; the aforesaid stem is contained in the activation compartment when the activator element is in the closed position.

Preferably, in preferred embodiments, the stem of the activator element may be of the elastic and/or flexible type and may have a substantially rhomboidal spring shape to facilitate the use thereof.

In addition, the head of the activator element may comprise one or more containment portions arranged above the closing portion.

In a preferred embodiment, the head may also comprise a sliding crown provided with one or more mixing means arranged above the containment portion of the activator element and being larger than the closing portion.

In detail, the aforesaid mixing means may be selected from at least one of the following types:
- through holes; and/or
- hooks obtained in the perimeter of the sliding crown itself; and/or
- lateral cuts obtained on the perimeter of the sliding crown; and/or
- triangles; and/or
- cross.

In addition, in further preferred embodiments, the head of the activator element may comprise one or more sliding crowns interposed between the containment portion and the above-mentioned sliding crown.

Further, the head of the activator element may comprise a relief arranged on the top to improve the mixing of the substances to be dispensed from the container the object of this invention.

In a preferred variant, the head of the activator element in question may have a locking area which may be made in different shapes and materials, so as to block a needle and/or another dispensing accessory which may be connected to the container to prevent reuse.

In addition, the container according to the invention may comprise a sealing insert arranged therein, having a substantially truncated cone shape, and having: one or more protrusions or perimeter recesses along the relative wall so as to promote the anchoring thereof at the second portion of the dispensing compartment, and a converging portion arranged between the activation compartment and the dispensing compartment, the activator element in this embodiment being hermetically engaged with the aforesaid converging portion when it is in closed position; the sealing insert and the activator element may be assembled and tested prior to the insertion into the container the object of this invention.

Further, in other preferred embodiments, the sealing insert may comprise a pair of levers arranged inside the activation compartment, each of which may be fixed to the outer surface of the converging portion or to the outer surface of the lateral surface, and may further comprise a hook relief such that when they are actuated, thus squeezing the activation compartment of the container, they interfere with the activator element, disengaging it from the converging portion of the sealing insert and causing the activator element to pass from the closed position to the open position.

Further, the sealing insert may comprise a trigger device connected to the sealing insert through tabs comprising a thrust member wherein, when the activation compartment is squeezed, the trigger device is moved in such a way as to cause the sealing area of the activator element to disengage from the converging portion of the sealing insert.

In other preferred but non-limiting embodiments, the activation compartment of the container the object of this invention may have a spheroidal or ellipsoidal shape, in particular to promote the squeezing thereof.

In addition, the activation compartment may comprise one or more bellows adapted to facilitate the compressibility thereof, in particular during the step of using the aforesaid container.

Further, the activation compartment of the container may have a shaped portion adapted to receive the free end of the stem of the activator element so as to guide and facilitate the translational movement thereof along the axis thereof.

In addition, the dispensing member may comprise a nozzle which may be arranged on the top thereof or on the lateral wall of the dispensing compartment;

a pair of nozzles, which are preferably arranged at a distance from each other such that the substance may be dispensed into the nostrils of a user's nose.

In preferred embodiments, the relief on the head of the activator element may be made of soft material, such as rubber and similar, to allow the same to be inserted at the base of an insert which is located either in the first portion of the dispensing compartment or in the nozzle, thereby avoiding possible reuse of the container, particularly when the activator element is in the open position.

The container according to this invention may be used for dispensing the at least one substance contained in the activation compartment and/or in the dispensing compartment by disengaging the activator element so as to fluid-dynamically connect the aforesaid compartments until a predefined threshold is reached; and by dispensing the at least one substance through at least one dispensing member of those described above.

In addition, the contents of the activation compartment may be mixed with the contents of the dispensing compartment both after the disengagement of the activator element and prior to opening the dispensing members.

In particular, mixing takes place by means of the above-mentioned mixing means of the sliding crown of the activator element.

Finally, the container the object of this invention may be made:
- by increasing the temperature of the container so that it is workable;
- by inserting the activator element into the container; and
- by centring and engaging the activator element between the activation compartment and the dispensing compartment.

Further, during the manufacturing steps of the aforementioned container, there may be a further step of inserting the sealing element into the container together with the activator element, the activator element may be pre-assembled inside the sealing element itself; this happens prior to centring and engaging the sealing insert in the container and prior to closing the container once it has been made.

In preferred embodiments, the activation compartment and/or said dispensing compartment are moulded using a "Blow Fill Seal" process.

BRIEF DESCRIPTION OF THE SEVERAL VIEWS OF THE DRAWINGS

Further features and advantages of the pre-filled container according to this invention will be more evident from the following description, referring to a preferred, but non-limiting, example embodiment, and from the accompanying drawings, wherein:

FIG. 1A shows a perspective view of a first embodiment of the pre-filled container according to this invention;

FIG. 1B is a sectional front view showing the pre-filled container of FIG. 1A, in closed configuration;

FIG. 1C is a sectional front view showing the pre-filled container of FIG. 1A, in open configuration;

FIG. 1D is a sectional front view showing the pre-filled container of FIG. 1A, in an intermediate configuration of use;

FIG. 1E shows the pre-filled container of FIG. 1A, in an end-of-use configuration;

FIG. 2A shows an isometric view of a first embodiment of the activator element of the pre-filled container the object of this invention;

FIG. 2B shows an isometric view of a second embodiment of the activator element of the pre-filled container the object of this invention;

FIG. 2C shows an isometric view of a third embodiment of the activator element of the pre-filled container the object of this invention;

FIG. 2D shows an isometric view of a fourth embodiment of the activator element of the pre-filled container the object of this invention;

FIG. 2E shows an isometric view of a fifth embodiment of the activator element of the pre-filled container the object of this invention;

FIG. 3A is a sectional front view of a first embodiment of the sealing insert coupled to an activator element;

FIG. 3B shows a sectional front view of a second embodiment of the pre-filled container according to this invention, in which the sealing insert and the activator element are coupled to the container in a possible closed configuration;

FIG. 3C is a sectional front view showing the pre-filled container of FIG. 3B, in a possible end-of-use configuration;

FIG. 4 schematically shows a sectional front view of a third embodiment of the pre-filled container according to this invention;

FIG. 5A shows an isometric view of a sixth embodiment of the activator element of the pre-filled container the object of this invention;

FIG. 5B shows a sectional front view of a fourth embodiment of the pre-filled container according to this invention, in a possible closed configuration;

FIG. 5C shows a sectional front view of the pre-filled container of FIG. 5B, in a possible open and intermediate configuration of use;

FIG. 5D shows a sectional front view of the pre-fillable container of FIG. 5B, in a possible end-of-use configuration;

FIG. 6A schematically and frontally shows a section of a second embodiment of the sealing insert for the activator element of a fifth embodiment of a pre-filled container according to this invention;

FIG. 6B schematically and frontally shows a section of the sealing insert for the activator element and the pre-filled container of FIG. 6A, in a possible configuration of use;

FIG. 7A shows a sectional front view of a sixth embodiment of the pre-filled container the object of this invention;

FIG. 7B shows a sectional front view of a seventh embodiment of the pre-filled container according to this invention;

FIG. 7C shows a sectional front view of an eighth embodiment of the pre-filled container according to this invention;

FIG. 7D shows a sectional front view of a ninth embodiment of the pre-filled container according to this invention;

FIG. 7E shows a sectional front view of a tenth embodiment of the pre-filled container according to this invention;

FIG. 7F shows a sectional front view of an eleventh embodiment of the pre-filled container according to this invention;

FIGS. 8A to 8E schematically show the steps of a particular use of the pre-filled container the object of this invention.

DESCRIPTION OF SPECIFIC EMBODIMENTS OF THE INVENTION

FIGS. 1A to 1D show a first embodiment of the pre-filled container, generically indicated by the numerical reference 1.

The container 1 comprises an activation compartment 2, a dispensing compartment 3 and an activator element 4.

The activation compartment 2 is made so as to be squeezable even by the pressure of a user's fingers, as will be explained in more detail below.

In the embodiment under consideration, said activation compartment 2 has a substantially globose shape, although different shapes or configurations may be provided in other embodiments.

The aforesaid activation compartment 2 comprises a weakened bellow area 21 at the middle area thereof, to facilitate the squeezing of the activation compartment 2 itself when it is squeezed.

Advantageously, the activation compartment 2 also has, on the base, a shaped portion 22 obtained as a recess on the relative inner surface, so that when the activation compartment 2 is squeezed to dispense the substance contained therein, the aforesaid shaped portion 2 facilitates the use, and thus the functioning, of the container 1, as further explained below.

The aforementioned activation compartment 2 may be moulded using the "Blow Fill Seal" (BFS) process. In particular, in preferred embodiments, the activation compartment 2 is made of substantially elastic materials, for example plastic or rubber, in such a way as to favour, as mentioned above, the squeezing thereof, as shown in FIGS. 1D and 1E. Thus, when the activation compartment 2 is squeezed by the user, a portion thereof collapses substantially onto itself, in the squeezing direction.

Generally, for sterility reasons, said activation compartment 2 is pre-filled with at least one substance or mixture to be dispensed.

It should be noted that also several substances or mixtures of substances, such as by way of example, air and/or other gases, to be dispensed simultaneously may also be inserted into said activation compartment 2.

The dispensing compartment 3 in this embodiment has a substantially tubular geometry, but may also take on other geometries and shapes, as will be shown in the following embodiments. Also the dispensing compartment 3 may also be made of substantially elastic and/or plastic materials, and also moulded using the BFS process.

Further, the dispensing compartment 3 may be pre-filled with at least one substance or mixture, such as also air, similarly to the activation compartment 2 which as seen below, is dispensed from the container 1.

Said dispensing compartment 3 comprises a first portion 31, equipped with at least one dispensing member 311, i.e. in the embodiment under consideration, a nozzle, which may advantageously be connected to accessories, such as e.g. needles, for dispensing the substances contained in the container 1, and a second portion 32 comprising a groove section 321, at which the dispensing compartment 3 itself is connected to the activation compartment 2.

There may be one or more shaped portions 322 in the second portion 32 of the dispensing compartment 3, which are adapted to improve the mixing of the liquid.

In particular, when the dispensing compartment 3 is made, also by means of the aforementioned BFS moulding process, said groove section 321 is moulded and calibrated by inserting the activator element 4 into the container 1.

More in detail, the activator element 4 is inserted when the materials forming the dispensing compartment 3, as said, for example of plastic type, are still malleable due to the temperatures of the aforementioned BFS process still underway, and therefore acts as a mould for calibrating the groove section 321.

Generally, the activator element 4 may be inserted before or after the mould is closed during the process of making the container.

In embodiments, the activator element 4 may be inserted either before or after the mould is closed in the BFS process.

In this way, given that it is complementary to the groove section 321, the activator element 4 has a greater seal therein, thus consequently increasing the degree of isolation between the dispensing compartment 2 and the activation compartment 3.

In the embodiment under consideration, the activator element 4 is arranged completely inside the container 1, wherein it is held in position to be subsequently moved or deformed between a closed position and an open position, as further explained below, in particular in the squeezing direction of the activation compartment 2, as further explained below.

The aforementioned activator element 4 may be made, for example of plastic materials and/or by moulding.

The activator element 4 also comprises a head 42, whose function is explained later.

Said head 42 of the aforesaid activator element 4 comprises a substantially tapered sealing portion 424 adapted to engage with the groove section 321 so as to hermetically isolate the contents of the activation compartment 2 and the dispensing compartment 3, respectively.

Moreover, said activator element 4 also comprises a stem 41 having substantially elongated shape, which is coupled below the sealing portion 424. In the embodiment under consideration, the stem 41 is arranged inside said activation compartment 2 when the activator element 4 is in the closed position.

In particular, the free end of said stem 41 of the activator element 4 is arranged at the shaped portion 22 of the activation compartment 2 in order to facilitate the use of the aforesaid container 1 during the dispensing of the at least one substance.

The aforesaid shaped portion 22 intercepts and receives the free end of the stem 41 when the activation compartment 2 is squeezed to dispense the substance contained in the activation compartment 2 itself.

Said stem 41 allows the squeezing force exerted on said activation compartment 2 to be transmitted to the activator element 4 itself. Furthermore, the length of the stem 41 determines the pressure inside the activation compartment 2 when said activator element 4 is disengaged from the groove section 321 of the dispensing compartment 3, due to said squeezing force.

The head 42, the sealing area 424 and the stem 41 of the activator element 4 in this embodiment are made in one piece, therefore moulded and made at the same time, or are of the pre-assembled type. In further embodiments not shown in the figures, the head 42, the sealing area 424 and the stem 41 may be moulded separately and with different materials, and thus be considered as different parts to be assembled prior to or after insertion.

The operation of the pre-filled container 1 according to the embodiment shown in FIG. 1B is as follows.

Prior to the use of the pre-filled container 1, the activator element 4 is in the closed position (FIG. 1B, 1C), in which the portion 424 is coupled to the pre-filled container 1, thus fully engaging the groove portion 321 and thus hermetically closing the fluid-dynamic connection between the activation compartment 2 and the dispensing compartment 3 so as to isolate the respective contents thereof.

Moreover, in the embodiment under consideration, in particular reference to FIGS. 1B and 1C, the dispensing compartment 3 has a removable closing seal 315, for example with a twist-off mechanism, adapted to keep the dispensing compartment 3, and possibly its contents, isolated from the external atmosphere until the moment the pre-filled container 1 is used.

In FIG. 1C, given that the container 1 is in open configuration, the closing seal 315 is removed, the dispensing nozzle 311 is exposed.

Subsequently, as shown in the exemplifying FIG. 1D, the user, gripping the activation compartment 2 with his/her fingers, squeezes it according to the direction L, reaching a position in which the surface of the portion 22 of said activation compartment 2 touches the lower part of the stem 41; at this point, the desired pressure for dispensing is created inside the container 2.

Subsequently, the user, while continuing to squeeze the compartment 2 according to the direction L, starts to move the stem 41 of said activator element 4 by disengaging the portion 424 of the activator element 4 from said groove section 321, as seen in FIG. 1E, so that the activator element 4 passes from said closed position to said open position, putting the activation compartment 2 and the dispensing compartment 3 into fluid-dynamic communication, causing the mixing of the substance/mixture of the activation compartment 2 with the product contained in said dispensing compartment 3.

Further, the substance or mixture contained in the indicated compartments thus leaves the nozzle 311 with considerable pressure, adapted for example, to be administered as a spray.

FIG. 2A shows a first embodiment of the activator element 4.

In particular, such activator element 4 comprises a closing portion 424 coupled to said stem 41 and to the head 42, intended to engage with said second portion 32 of the dispensing compartment 3, at the groove section 321, when said activator element 4 is in the closed position.

The head 42 of such activator element comprises a sliding crown 422 which is, for example circular in shape, is larger than said closing portion 424, and comprising mixing means which in this case, are through holes 4221 adapted to mix the substance to be dispensed and sprayed.

Said sliding crown 422 also acts as a guide for the activator element 4 during the movement thereof, as seen in FIGS. 1D and 1E.

Said head 42 of said activator element 4 also contains an area 421 that is substantially cylindrical in shape, which may allow the substance to be dispensed to be placed between the sliding crown and the closing portion 424 so as to improve the mixing thereof.

The head 42 under consideration also comprises a relief 423 arranged above said sliding crown 422 and intended to improve mixing.

Again advantageously, the aforesaid relief 423 and a portion relative to the aforesaid stem 41 may be used for the transport of said container 1.

The stem 41 in the aforesaid embodiment has a substantially cross-shaped section so as to favour the passage of the at least one substance from said activation compartment 2 to said dispensing compartment 3. As said, the stem 41 is adapted to transmit the squeezing force from said activation compartment 2 to the activator element 4, to dose the amount of the at least one substance to be dispensed and to regulate the pressure inside the activation compartment 2 when the sealing area 424 of said activator element 4 is disengaged from the groove section 321 of said container 1.

FIG. 2B shows a second embodiment of the activator element 4, wherein the sliding crown 422 has no mixing holes and the stem 41 has a cylindrical shape, for example to give said stem 41 of said activator element 4 greater rigidity.

The activator element 4 of the embodiment described herein is the one depicted in FIGS. 1A to 1E.

FIG. 2C shows a third embodiment of the activator element 4, wherein the sliding crown 422 has mixing hooks 4222 located along the perimeter of the crown 422 itself and adapted to also create turbulence as the substance to be dispensed passes so as to improve mixing.

The stem 41 in the aforesaid embodiment is substantially identical to that described in the first embodiment, in particular in FIG. 2A.

FIG. 2D shows a fourth embodiment of the activator element 4.

In the embodiment under consideration, the sliding crown 422 is connected below a further sliding crown 425, which is adapted to improve the mixing and dispensing process of the substance from said pre-filled container 1. The further sliding crown 425 is coupled to said portion 421 of the head 42, which is connected in turn to said closing portion 424.

Similarly to that described for the previous embodiments, the closing portion 424 is connected to the stem 41 of the activator element 4.

FIG. 2E shows a fifth embodiment of such activator element 4. The sliding crown 422 has lateral cuts 4223 to improve the passage of the mixture. There is an area 425 in the head 42 that may also be made of a different material, for example rubbery, which allows a needle or other accessory to be jammed and prevent reuse, which will be explained later.

FIG. 3A shows a first embodiment of the sealing insert 5 coupled to an activator element.

In the embodiment under consideration and with particular reference to FIG. 3B, both the activation compartment 2 and the dispensing compartment 3 are substantially similar to what is described, for example with reference to the embodiment of the pre-filled container 1 shown in FIGS. 1A-1E.

The dispensing compartment 3 does not have the groove 321; in the embodiment under consideration, the aforesaid dispensing compartment 3 is not fluid-dynamically connected to the activation compartment 2 since the sealing insert 5 is between them. In this embodiment, the activator element 4 moves inside the aforementioned sealing insert 5, for example in the shape of a truncated cone, it also located inside the pre-filled container 1, prepared to ensure a more controlled and uniform movement of the activator element 4 during the step of using the pre-filled container 1.

The sealing insert 5 could comprise one or more protrusions or perimeter recesses 52 located along the outer surface 53 of said insert to allow greater anchorage when such sealing insert is inserted into the pre-filled container 1 at the portion 32 of the dispensing element 3.

Such lateral wall 53 may have a cylindrical or truncated cone shape, for example, as depicted in particular in FIGS. 3A and 3B.

A converging portion 51 arranged in use between the activation compartment 2 and the dispensing compartment 3 defining the section of area separating the two compartments, is provided on the lower edge of said lateral wall 53. The inner surface of said converging portion 51 performs substantially the same function as the groove section 321, which is present, for example in the embodiment of the pre-filled container 1 shown in FIG. 1.

In preferred embodiments, said sealing insert 5 may be pre-assembled to the activator element 4 to allow a seal check before being inserted into said pre-filled container 1, if necessary.

If said activator element 4 is coupled to said sealing insert 5 prior to the insertion into said container 1, it is possible to couple them with a system that ensures accurate calibration of the sealing force between such activator element and such sealing insert to also ensure an accurate decoupling force. As shown in FIG. 3C, the lower walls of the activation compartment collapse towards the inside of the pre-filled container 1 through the squeezing by the user of the activation compartment 2 in the direction L. In other words, in this embodiment, part of the activation compartment 2 changes from concave to convex. Further, thanks to the shape and deformability of the activation compartment 2, the inner walls of the latter remain adjacent, allowing the dispensing of the entire substance contained therein and at the same time avoiding any risk of reflux, i.e. the return of part of the substance dispensed inside container 1, after the user releases the container. The configuration described above effectively prevents the reuse of the pre-filled container 1 and facilitates and improves the dispensing reliability of the substance or mixture contained in the latter.

FIG. 4 describes a further embodiment of the pre-filled container 1, wherein the activator element 4 comprises only the head 42 and the tapered part 424 intended to engage with the converging portion 51 of the sealing insert 5.

In this embodiment, the sealing insert 5 comprises a trigger device 54, which is contained in said activation compartment 2 when the activator element 4 is in the resting position. Said trigger device 54 comprises a thrust member 512.

The contents inside said activation compartment 2 are pressurised during the squeezing of the activation compartment 2 in the direction L.

Continuing the squeezing of the activation compartment 2 in the direction L, the thrust member 512 of the trigger device 54 moves the head 42 of the activator element 4, disengaging the same from the portion 51 of said sealing insert, putting the contents of the activation compartment 2 and the contents of the dispensing compartment 3 in fluid-dynamic communication, thus causing the dispensing of the mixture at the desired pressure.

FIG. 5A shows a sixth embodiment of the activator element 4.

The activator element 4 has a tapered sealing area 424 adapted, as described above, to engage the aforementioned groove section 321 so as to hermetically isolate the contents of the activation compartment 2 and the dispensing compartment 3, respectively.

In the embodiment under consideration, the sealing area 424 of the activator element 4 is connected below an elastic stem 411 having a substantially rhomboidal spring shape, in such a way as to facilitate or favour the squeezing process of the activation compartment 2 itself, by the user.

In particular, in the case under consideration, the sliding crown 422 of the activator element 4 has a substantially circular surface that has mixing means, in particular, lateral cuts 4223 to improve mixing.

The pre-filled container 1 depicted in FIGS. 5A to 5D has a dispensing compartment 3 which is substantially the one described in the figures in the previous embodiments, while the activation compartment 2 has, in the embodiment depicted, a quadrangular shape such as to allow the lateral squeezing thereof in the direction R shown in the analysed figures. The activation compartment 2 may also take on other shapes than the quadrangular one, as required.

As may be verified in detail in FIGS. 5A to 5D, the operating mechanism allows the user to compress the activation compartment 2 during use, laterally in the squeezing direction R.

During the squeezing of the activation compartment 2, the internal pressure thereof increases until the inner surface which is pushed, for example, by the user's fingers, begins to press on the stem 411, thus causing the sealing area 424 of said activator element 4 to decouple from the groove section 321 of said container 1. Following this decoupling, substantially what has already been described in FIG. 1C takes place, namely the dispensing of the at least one substance contained in container 1.

FIGS. 6A and 6B show a second embodiment of the sealing insert 5, inside which the same is arranged in a simplified manner in a pre-filled container 1 like the one in the embodiment described above.

As shown, the shuttle 5 has, connected to the converging portion 51, a pair of levers 512 arranged inside the activation compartment 2 of the pre-filled container 1. Each of said levers 512 is fixed at one end to the converging portion 51 of said shuttle 5 and comprises a hook relief 513, the function of which is further described below.

As with other embodiments, when using the pre-filled container 1, the activation compartment 2 must be squeezed here too, particularly on the lateral walls, according to the arrows indicated by letter R in FIG. 6B. The pair of levers 512 is actuated so that each of the hook reliefs 513 interferes with the base of the sealing area 424 of the activator element 4, disengaging it from the converging portion 51, putting the contents of the activation compartment 2 and the dispensing compartment 3 into fluid-dynamic communication; moreover, the relative internal pressure is raised by means of the pressure applied on the sides of the activation compartment 2 so that when said activator element 4 is disengaged from the converging portion 51, the same dispensing process described in the previous embodiments takes place.

FIG. 7A shows a sixth embodiment of the pre-filled container 1.

In the embodiment under consideration, in addition to what has been described above, the activation compartment 2 comprises, in positions parallel to a middle area thereof, multiple weakened bellow areas 211 adapted to facilitate the squeezing process.

FIG. 7B shows a seventh embodiment of the pre-filled container the object of this invention, in which the dispensing compartment 3 includes, in the first portion 31, a further nozzle 312, additional to the nozzle 311, which is adapted, for example to facilitate use when the at least one substance must be dispensed in both nostrils of a patient, in order to make the process in question simpler and highly ergonomic.

Moreover, the activator element is of the type shown in FIG. 2B also in the embodiment described above.

The operation of the pre-filled container 1 according to the aforementioned third embodiment is substantially similar to that described above, with the additional feature given by the fact that, in the step of using the pre-filled container 1, the substance will be dispensed simultaneously through the two nozzles 311 and 312.

FIG. 7C shows an eighth embodiment of the pre-filled container 1, wherein the dispensing compartment 3 comprises a tilted portion 33 on which the nozzle 311 is located so as to be more ergonomic, especially for nasal applications.

The operation of the pre-filled container 1 according to the above-mentioned second embodiment is substantially as described above.

During the step of using the container 1, the tilted portion 33 of the dispensing compartment 3 allows the user to place one finger in the area 331 and one finger below the activation compartment 2, in the area indicated by number 221, thus facilitating and making the grip and subsequently the application, easier and more ergonomic.

FIG. 7D shows a ninth embodiment of the pre-filled container 1, wherein in addition to what was described above, in particular in the first embodiment of the container 1, the activation compartment 2 has a shape that is substantially ellipsoidal and is in an offset position with respect to the dispensing compartment 3.

The offset position of the activation compartment 2 during use allows squeezing to be carried out by two fingers placed on the areas indicated by numbers 222 and 221 in the activation compartment 2 itself, thus effectively decreasing the effort necessary for dispensing the at least one substance from the container 1.

FIG. 7E shows a tenth embodiment of the pre-filled container 1, wherein the dispensing compartment 3 comprises an additional portion 331 arranged laterally to the dispensing compartment 3 and at the second section 31, on which there is the nozzle 311 which, as shown in FIG. 22A, has the cap 315, similarly to what was said above, adapted to isolate the contents of the container 1 from the atmosphere.

This design makes the system ergonomic for the user to grip, especially for nasal applications.

The operation of the pre-filled container 1 is the same as the one for the embodiments described above. In particular, the additional portion 331 of the dispensing compartment 3 allows the user to position one finger at the portion 222 of the dispensing element 3 and one finger below the activation compartment 2, numbered 221, during use, thus making this specific application easier.

FIG. 7F shows an eleventh embodiment of the container 1, wherein the dispensing compartment 3 comprises two additional portions 331 located laterally with respect to the dispensing element 3, on which there is a first nozzle 311 and a second nozzle 312, respectively, so as to be more ergonomic, especially for nasal applications. The grip is substantially the same as that described for FIG. 7E, so one finger may be positioned in the area 221, while the other may be positioned in the area 222. During use, the substance contained in the pre-filled container 1 is simultaneously dispensed, for example, as mentioned, into the patient's nostrils by means of the two nozzles 311 and 312.

FIGS. 8A to 8E describe using, in a further embodiment, the pre-filled container 1, which provides a dispensing element, for example a needle 314.

The use of such container is substantially the same as that described for FIG. 1.

The activator element shown is substantially the same as the one depicted in FIG. 2E.

It should be noted that the container 1 according to this invention may also be pre-fillable, i.e. the substances to be dispensed may possibly be inserted into the activation compartment 2 or dispensing compartment 3 after the container 1 itself has been made.

Advantages

The pre-filled container as described above and in accordance with the examples illustrated in detail in accompanying FIGS. 1 to 8, has several advantages in particular; the invention thus conceived also makes it possible to create a disposable pre-filled, sterile container which allows the substances contained therein to be administered in the form of a spray; further, it ensures:

simplicity, functionality and speed of assembly and use;
accuracy in the release of the medication;
reliability and safety in use, as compared to known solutions;
suitability for containing different types of liquids, and therefore medicines/pharmaceuticals;
safety from the point of view of contamination;
if required, certainty of non-reuse of the container;
impossibility of counterfeiting the product;
versatility and adaptability to a multitude of situations and volumes of liquid to be contained;
limited cost, as compared to traditional solutions, in relation to the benefits achieved.

The invention described may be modified and adapted in several ways without thereby departing from the scope of the inventive concept.

Moreover, all the details may be replaced by other technically-equivalent elements.

Lastly, providing they are compatible with the specific use, the components used, as well as the dimensions, may vary according to requirements and the prior art.

Where the features and the techniques mentioned in the following claims are followed by reference signs, the reference signs have been used only with the aim of increasing the intelligibility of the claims themselves and, consequently, the reference signs do not constitute in any way a limitation to the interpretation of each element identified, purely by way of example, by the reference signs.

The invention claimed is:

1. A production method of a pre-filled or pre-fillable with one or more substances, comprising:
    a squeezable activation compartment for containing said substances;
    a dispensing compartment with a first portion having at least one dispensing member and a second portion fluid-dynamically connected to the activation compartment;
    an activator element inside a container, having a head with a tapered closing portion and a sliding crown larger than the tapered closing portion, the sliding crown provided with one or more mixing elements;
    wherein the activator element is movable between a closed position, hermetically isolating the activation compartment from the dispensing compartment, and an open position, allowing fluid-dynamic communication between the compartments for substance dispensing;
    wherein the production method comprising:
    comprising the following steps:
    increasing a temperature of said container for workability;
    inserting said activator element into said container; and
    centring and engaging said activator element between said activation compartment and said dispensing compartment
    wherein at least one of the activation compartments and the dispensing compartments are molded by a "Blow Fill Seal" process; and
    wherein the dispensing and activation compartments are formed and calibrated by inserting the activator element into the container.

2. The method according to claim 1, wherein it comprises the further step of inserting said sealing insert into said container with said activator element pre-assembled in said sealing insert before centring and engaging said sealing insert in said container and before closing said container.

3. The method according to claim 2, wherein said activator element passes from said closed position to said open position when said activation compartment is squeezed.

4. The method according to claim 1, wherein said activation compartment is configured so that when it is squeezed, it interferes with said activator element to allow the movement thereof.

5. The method according to claim 1, wherein said activator element comprises a stem coupled below said closing portion, contained in said activation compartment when said activator element is in said closed position.

6. The method according to claim 5, wherein said stem is elastic and/or flexible and has a substantially rhomboidal spring shape.

7. The method according to claim 5, wherein said activation compartment has a shaped portion adapted to receive the free end of said stem of said activator element so as to guide the translational movement thereof along the axis thereof.

8. The method according to claim 5, wherein said head comprises one or more containment portions arranged above said closing portion, opposite to said stem.

9. The method according to claim 8, wherein said head comprises one or more sliding crowns interposed between said containment portion and said sliding crown.

10. The method according to claim 1, wherein said mixing means are selected from at least one of the following:
    through holes; and/or
    hooks obtained on the perimeter of said sliding crown; and/or
    lateral cuts obtained on the perimeter of said sliding crown; and/or
    triangles; and/or
    cross.

11. The method according to claim 1, wherein said head comprises a relief arranged on the top to improve the mixing of said at least one substance to be dispensed.

12. The method according to claim 11, wherein said relief is made of soft material, such as rubber and similar, to allow it to be inserted at the base of an insert positioned in said first portion or into the nozzle, and to avoid the reuse of the container when said activator element is in said open position.

13. The method according to claim 1, wherein said head has a locking area which may be made in different shapes and materials, for blocking a needle and/or another dispensing accessory for dispensing said at least one substance to be dispensed, connected to said container, to prevent reuse.

14. The method according to claim 1, wherein the container comprises a sealing insert having a substantially truncated cone shape, arranged inside said container and having
    one or more protrusions or perimeter recesses along the lateral wall, for anchoring at said portion, and
    a converging portion arranged between said activation compartment and said dispensing compartment,
    wherein said activator element is hermetically engaged with said converging portion when it is in said closed position,
    wherein said sealing insert and said activator element may be assembled and tested before the insertion into the container.

15. The method to claim 14, wherein said sealing insert comprises a pair of levers arranged inside said activation compartment, and in that each of said levers is fixed to the external surface of the converging portion or to the external surface of the lateral wall and comprises a hook relief so that when said levers operated by squeezing said activation compartment, said hook reliefs interfere with said activator element, disengaging it from said converging portion by passing said activator element from said closed position to said open position.

16. The method according to claim 14, wherein said sealing insert comprises a trigger device connected to said sealing insert through one or more tabs and having a thrust member,
   wherein when the activation compartment is squeezed, said trigger device is moved so that said thrust member causes the disengagement of said sealing area of said activator element from said converging portion.

17. The method according to claim 1, wherein said activation compartment has a spheroidal or ellipsoidal shape.

18. The method according to claim 1, wherein said activation compartment comprises one or more bellows to facilitate the compressibility thereof.

19. The method according to claim 1, wherein said at least one dispensing member comprises:
   a nozzle arranged on the top or on the lateral wall of said dispensing compartment; or
   a pair of nozzles which are preferably arranged at a distance such as to allow the dispensing of the substance to be dispensed into the nostrils of a user's nose.

20. A method for dispensing at least one substance through the container produced according to the production method of claim 1, wherein said substance is contained in said activation compartment and/or in said dispensing compartment, comprising the following steps:
   disengaging said activator element so as to fluid-dynamically connect said activation compartment and said dispensing compartment upon reaching a predefined threshold; and
   dispensing said at least one substance through said at least one dispensing member.

21. The method according to claim 20, wherein it comprises the step of mixing the content of said activation compartment with that of said dispensing compartment following the disengagement of said activator element.

22. The method according to claim 20, wherein the method comprises the step of mixing the contents of said activation compartment with that of said dispensing compartment following the disengagement of said activator element and prior to the opening of such one or more dispensing members.

23. The method according to claim 22, wherein said mixing takes place by means of said mixing means of said sliding crown.

\* \* \* \* \*